United States Patent
Reich et al.

(10) Patent No.: US 8,339,599 B2
(45) Date of Patent: Dec. 25, 2012

(54) MEASURING ARRANGEMENT FOR AN OPTICAL SPECTROMETER

(75) Inventors: Oliver Reich, Potsdam (DE);
Hans-Gerd Löhmannsröben, Postdam-Golm (DE)

(73) Assignee: Universitaet Potsdam (DE)

( * ) Notice: Subject to any disclaimer, the term of this patent is extended or adjusted under 35 U.S.C. 154(b) by 318 days.

(21) Appl. No.: 12/679,614

(22) PCT Filed: Sep. 18, 2008

(86) PCT No.: PCT/EP2008/007828
§ 371 (c)(1),
(2), (4) Date: May 11, 2010

(87) PCT Pub. No.: WO2009/040055
PCT Pub. Date: Apr. 2, 2009

(65) Prior Publication Data
US 2010/0284004 A1 Nov. 11, 2010

(30) Foreign Application Priority Data
Sep. 24, 2007 (EP) .................................. 07018676

(51) Int. Cl.
*G01J 3/30* (2006.01)
(52) U.S. Cl. .................. 356/317; 356/319; 356/326
(58) Field of Classification Search .......... 356/317–319, 356/328, 73, 326, 445; 250/281, 288, 287; 422/82.08; 436/172
See application file for complete search history.

(56) References Cited

U.S. PATENT DOCUMENTS

| | | | |
|---|---|---|---|
| 5,452,723 A | 9/1995 | Wu et al. | |
| 5,987,351 A | 11/1999 | Chance | |
| 6,016,435 A * | 1/2000 | Maruo et al. | 600/316 |
| 6,069,689 A * | 5/2000 | Zeng et al. | 356/73 |
| 6,138,082 A * | 10/2000 | Wang et al. | 702/109 |
| 6,525,820 B1 * | 2/2003 | Owens | 356/450 |
| 7,054,002 B1 | 5/2006 | Sevick-Muraca | |
| 7,088,495 B2 * | 8/2006 | Trepagnier et al. | 359/326 |
| 2004/0022684 A1 * | 2/2004 | Heinze et al. | 422/82.08 |
| 2004/0036018 A1 * | 2/2004 | Deguchi et al. | 250/281 |
| 2005/0051428 A1 * | 3/2005 | Gabriel | 204/452 |
| 2006/0089556 A1 | 4/2006 | Bambot et al. | |

* cited by examiner

*Primary Examiner* — Sang Nguyen
(74) *Attorney, Agent, or Firm* — Schmeiser, Olsen & Watts, LLP

(57) ABSTRACT

The invention relates to a measuring arrangement for an optical spectrometer, in particular a photon density wave spectrometer, having a measuring chamber, which can be loaded with a sample to be measured, and a coupling-in/coupling-out device which is configured to receive excitation light from a light source and couple it into the sample to be measured in the measuring chamber and to receive measuring light formed in the sample to be measured on account of the excitation light which has been coupled in and to emit said measuring light to a detection device, wherein the coupling-in/coupling-out device has an optical switching device and a plurality of light guide elements which couple to the latter, have a respective optical waveguide and can be connected according to at least one selectable measuring configuration using the optical switching device in order to couple in the excitation light and receive the measuring light according to the at least one selectable measuring configuration, and wherein outputs of the plurality of light guide elements are positioned according to a spiral arrangement in the viewing direction of the outputs.

10 Claims, 1 Drawing Sheet

MEASURING ARRANGEMENT FOR AN OPTICAL SPECTROMETER

Figure 1:
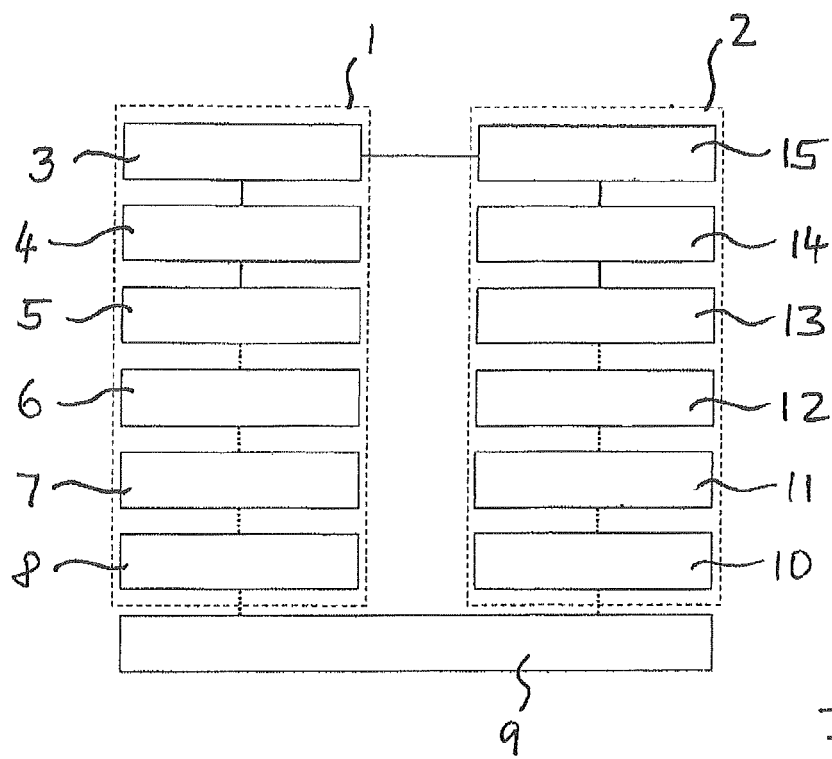

The invention relates to a measuring arrangement for an optical spectrometer, in particular a photon density wave spectrometer.

BACKGROUND OF THE INVENTION

Spectrometers are generally measuring or analysis devices for the spectroscopic investigation of a sample. Optical spectrometers use light for the spectroscopic investigation. Spectroscopic investigations with photon density waves permit the separate absolute determination of absorption and scattering properties of strongly scattering samples, which is not possible with conventional methods of light scattering or of absorption spectroscopy. The term "photon density waves" means the time- and space-dependent propagation of light in a strongly scattering medium, which is characterized by the number of photons per volume, i.e. the photon density.

The description of photon propagation is based on investigations of the transport of neutrons, as both photons and neutrons are uncharged and, apart from scattering processes, move freely of external forces. However, the description is simplified considerably for photons because, in contrast to neutrons, they all have a constant, equal velocity. Starting from the radiation transfer equation, in which all contributions that lead to a change in light intensity are balanced, generally an expansion to a series of spherical harmonics is used, in order to obtain a simple description of photon density. Similarly to particle transport, an optical diffusion coefficient appears as a characteristic quantity, and is described by absorption and scattering properties of the medium.

As the propagation of light is affected characteristically by absorption and scattering, analysis of photon density waves can be used for determining these optical properties. The known experimental techniques for utilizing photon density waves can be classified on the basis of the time dependence of the incident light used in each case. On the one hand, for investigations in the time domain, a very short light pulse is irradiated into the medium, and then the space-dependent time dependence of light propagation is monitored. On the other hand, for experiments in the frequency domain, light sources are used whose intensity can be modulated sinusoidally. Furthermore, investigations can also be carried out with time-constant light sources.

Spectroscopy based on photon density waves is suitable in particular for investigating strongly scattering media with relatively low absorption. On the one hand high scattering permits light propagation to be described as random particle transport. On the other hand, when there is strong absorption the photon density decreases so much that detection is difficult. Investigations by means of photon density waves are therefore often carried out in a spectral range from 600 to 900 nm, where many materials only display moderate absorption. Scattering is caused by local variation of the refractive index and is especially pronounced when the scale of magnitude of the variation corresponds to the wavelength of the light and the difference in refractive index is large. In particular, therefore, dispersions of materials with different refractive index, whose disperse phase consists of particles with a diameter of over 50 nm, display pronounced scattering in the visible region of the spectrum.

In a spectrometer for investigating a sample by means of photon density waves, usually excitation light, which is produced by a light source, for example a laser, is coupled onto the sample to be investigated by a coupling-in device. This takes place for example using an optical waveguide in the coupling-in device. A coupling-out device is then used for coupling-out measurement light arising in the sample to be investigated owing to the incident excitation light and feeding it to a detection device. The coupling-out device can also be formed using one or more optical waveguides, into which the measurement light is coupled-in, in order to guide it to the detection device. Based on considerations of physical models, the detected measurement light can be evaluated, in order to determine optical properties of the sample to be investigated.

The coupling-in of the excitation light and the coupling-out of the measurement light require particular attention, in order to receive measurement light signals that can actually be evaluated.

SUMMARY OF THE INVENTION

The object of the invention is to provide a measuring arrangement for an optical spectrometer, in particular a photon density wave spectrometer, with improved light coupling-in and coupling-out properties.

This problem is solved according to the invention with a measuring arrangement for an optical spectrometer according to independent claim 1. Advantageous variants of the invention are the object of dependent subclaims.

The invention comprises the concept of a measuring arrangement for an optical spectrometer, in particular a photon density wave spectrometer, with a measuring chamber, which can be loaded with a sample to be measured, and a coupling-in/coupling-out device, which is configured to receive excitation light from a light source and couple it onto the sample to be measured in the measuring chamber and to receive measurement light formed in the sample to be measured on account of the coupled-in excitation light and deliver it to a detection device, wherein the coupling-in/coupling-out device has an optical switching device and a plurality of optical waveguide elements coupled thereto with a respective optical waveguide that is connectable by the optical switching device according to at least one selectable measurement configuration, in order to couple-in the excitation light corresponding to the at least one selectable measurement configuration and to receive the measurement light, and wherein outputs of the plurality of optical waveguide elements are positioned corresponding to a spiral-shaped arrangement in the viewing direction towards the outputs.

It was found, surprisingly, that the spiral-shaped arrangement of the outputs of the plurality of optical waveguide elements particularly supports efficient coupling-in of the excitation light and efficient coupling-out of the measurement light. Crosstalk effects between the plurality of optical waveguide elements are minimized. Furthermore, the proposed arrangement of the plurality of optical waveguide elements supports a minimally disturbed light propagation in the sample to be measured by the optical waveguide or waveguides, which couple-in the excitation light, to the optical waveguide or waveguides which receive the measurement light. In this way the number of optical waveguides used can be increased, so that a large range of accessible distances is produced, with the result that it can be used for samples with very different optical properties.

Depending on the measurement configuration, the plurality of optical waveguide elements can be set up by means of the optical switching device within the scope of a measuring task so that both the excitation light is coupled-in on the sample to be measured and the measurement light is coupled-out. For example, each of the plurality of optical waveguide elements can be used successively for coupling-in the excitation light and for receiving the measurement light, wherein the optical switching device provides a corresponding optical connection of the plurality of optical waveguide elements. As an alternative, it can also be provided that one of the plurality of optical waveguide elements is connected for the duration of the measurement for coupling-in of the excitation light, whereas some or all of the remaining optical waveguide elements serve for receiving measurement light and conveying it on to the detection device. A selected connection, which corresponds to one measurement configuration, can remain unaltered for the duration of a measurement that is to be performed. In another embodiment the measurement configuration changes once or plurality of times in the course of a measurement. Depending on the connection of the individual optical waveguide element, a particular type of light, namely excitation light or measurement light, is conveyed by the associated optical waveguide. In accordance with the above account, a method of spectroscopic investigation of a sample, in particular investigation by means of photon density waves, can be implemented in various embodiments.

Optical switching devices are known per se, for example in the form of fibre-fibre switches, with which fibre ends of optical waveguides can be positioned relative to one another so that a transfer of light from one fibre end into another fibre end either takes place or does not. Such optical switching devices use for example translation slides, to displace the fibre ends relative to one another. The proposed measuring arrangement can be implemented, depending on the particular application, using various optical switching devices.

A preferred further embodiment of the invention provides that the outputs of the plurality of optical waveguide elements are arranged at different distances relative to a reference level transversely to the light exit direction of the excitation light from the outputs. Along the direction of propagation of the excitation light, the outputs are thus formed offset relative to one another. It can also be envisaged that at least two of the outputs are arranged at the same distance from the reference level, whereas at least one other output is displaced relative to this.

In an advantageous variant of the invention, it can be provided that the outputs of the plurality of optical waveguide elements are fixed in their position relative to one another at least for the at least one measurement configuration. The fixing of the outputs of the plurality of optical waveguide elements relative to one another can be designed to be permanent. Alternatively it can be envisaged that the outputs of the plurality of optical waveguide elements are movable relative to one another, for example by displacement, so that the relative positions between different measurements or even for different measuring steps within a measurement can be newly set, but are then in a fixed position. A displacement relative to one another of the outputs of the plurality of optical waveguide elements can for example be carried out by means of suitable translation slides, which in embodiments that are known per se can also achieve the necessary precision of said relative displacement.

An advantageous embodiment of the invention provides that at least one part of the outputs of the plurality of optical waveguide elements is arranged in the measuring chamber. This makes it possible for the part of the outputs of the plurality of optical waveguide elements that is arranged in the measuring chamber, is even immersed in the sample to be investigated, which can additionally be influenced in that the degree of filling of the measuring chamber is adjusted depending on the application. This can be provided for some or all of the outputs arranged in the measuring chamber, depending on the measuring task.

Preferably, a further embodiment of the invention provides that the part of the optical waveguide elements for which the output is arranged in the measuring chamber is led, fluid-tight, through a section of the wall of the measuring chamber. In a fluid-tight wall bushing, the optical waveguide elements can be arranged so that they are fixed or displaceable, for example by pushing or pulling. For example, the optical waveguide element is led as an optical waveguide in a seal made of an elastic material such as vulcanized or unvulcanized rubber.

In an advantageous variant of the invention it can be envisaged that the outputs of the plurality of optical waveguide elements are formed by optical waveguide outputs of the optical waveguides. As an alternative, the optical waveguide outputs can be preceded by optical elements, which in their turn then form the direct output for the optical waveguide element, through which the excitation light exits or the measurement light enters. In this connection it is possible to provide for example lenses or lens systems, which then form the direct output.

Another embodiment of the invention can envisage that the optical waveguides are formed from optical waveguides with a graded-index profile. The use of optical waveguides with a graded-index profile makes it possible to reduce demodulation and hence improve the measurement light quality at higher frequencies of light modulation or the use of longer optical waveguides.

A preferred further embodiment of the invention envisages that the optical waveguides are formed from photonic crystal fibres. For example, photonic crystal fibres of a so-called hollow-core design can be used.

In an advantageous embodiment of the invention it can be envisaged that the optical waveguides are produced according to at least one of the following designs: deuterated optical waveguides and fluorinated optical waveguides. The use of fibre-optic conductors with deuteration and/or a fluorination makes it possible to reduce absorption and therefore they can be used in a wider spectral range. Moreover, the reduced surface energy of fluorinated materials leads to less soiling of the optical waveguide and easier cleaning.

Optical waveguides can also be provided that incorporate a plurality of the aforementioned variants in any combination.

DESCRIPTION OF PREFERRED EXAMPLES OF THE INVENTION

Figure 2:
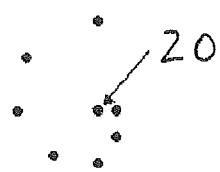
Figure 3:
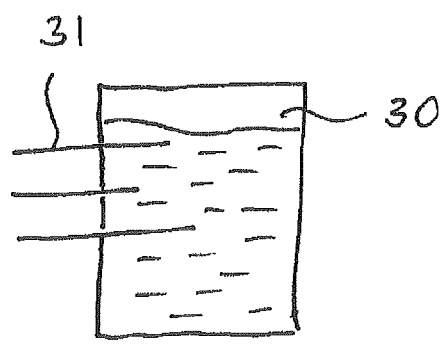

The invention is explained in more detail below, based on preferred examples, referring to the diagrams in a drawing, showing:

FIG. 1 a schematic representation of a measuring instrument using a photon density wave spectrometer, FIG. 2 a spiral-shaped arrangement of outputs of a plurality of optical waveguide elements in the viewing direction towards the outputs and FIG. 3 a schematic representation with a measuring chamber and a plurality of optical waveguide elements, whose outputs are arranged in the measuring chamber.

FIG. 1 shows a schematic representation of a measuring instrument using a photon density wave spectrometer (PDW-spectrometer). The dotted lines between the boxes relate to the transfer of optical signals, and continuous lines between the boxes relate to the transfer of electrical signals.

The measuring instrument is divided conceptually into two parts, namely an emission unit 1 and a detection unit 2. By means of the emission unit 1, a time-dependent electrical signal, which for example has a sinusoidal shape, is produced using a frequency generator 3. The frequency generator 3 produces a modulated electrical signal at an adjustable frequency. The frequency is in the range from a few kilohertz up to a plurality of gigahertz.

By means of signal conditioning 4 on the emission side, the electrical signal obtained by the frequency generator 3 is conditioned and is fed to a radiation source 5 which can be modulated, and which converts the signal received into a time-dependent optical excitation light. Depending on the radiation source, the electrical signal is conditioned first. Along with possible amplification, a time-independent signal is added, in particular via a biased-T. If a plurality of radiation sources is to be modulated, an electronic high-frequency switch can be provided for controlled switching of the signal to the individual radiation sources.

The radiation source 5 that can be modulated is for example a laser, in particular one or more diode lasers. The intensity of the latter can be modulated directly via the laser current. Furthermore, the diode lasers are temperature-stabilized and their intensity is monitored by a monitor diode. The radiation source 5 is shielded against entry and exit of electromagnetic radiation.

The excitation light produced is fed, after conditioning by beam conditioning 6 on the emission side, via radiation transporting means 7 on the emission side, to a coupling-in device 8, whose time-dependent modulated excitation light is then coupled-in on a sample to be measured in a measuring chamber 9. The radiation is transported to the sample via optical waveguides. A slight demodulation, in particular at high frequencies, and a slight absorption at the corresponding wavelength, are taken into account. By means of the optical waveguides, it is possible to have considerable distances between the radiation source 5 and the sample in the measuring chamber 9. Use of optical waveguides with a graded-index profile or photonic crystal fibres, for example of hollow-core design, makes it possible to reduce the demodulation and therefore improve the measuring signal at higher frequencies or the use of longer optical waveguides. The use of fluorinated and/or deuterated fibre-optic conductors makes it possible to reduce the absorption and therefore give a wider spectral range of use. Moreover, the decreased surface energy of fluorinated materials results in less soiling of the optical waveguides and easier cleaning.

In the detection unit 2, measurement light, which is produced in the sample owing to the coupling-in of the time-dependent excitation light, is coupled-out by means of a coupling-out device 10, which in its turn is of integrated design, being integrated with the coupling-in device 8, and is conducted via radiation transporting means 11 on the detection side to a beam conditioning 12 on the detection side and then to a detector 13. The coupling-out from the sample once again takes place via one or more optical waveguides. These are switched, via an optical switch, to a common optical waveguide or their position in the sample is altered appropriately by means of a translation slide. The further transport of radiation from the sample takes place via an optical waveguide. The above explanations of the radiation transport of the excitation light to the sample apply correspondingly.

The measurement light radiation to be detected is further conditioned in accordance with the requirements of the particular application. Thus, in addition to spectral filtering by means of an (interference) filter, it can also be split by means of dichroic mirrors onto a plurality of detectors. For this, usually the optical signal from the optical waveguide is first parallelized via a lens (not shown).

The measurement light received is finally converted by detector 13 into an electrical measuring signal, which in its turn is then conditioned by means of a signal conditioning on the detection side, and it is finally fed to a phase-sensitive detector 15. Depending on the spectral region and other conditions, the optical signal is converted to an electrical signal via avalanche or PIN diodes or photomultipliers. Apart from the temporal resolution and spectral sensitivity, a further linear region, little amplitude-phase crosstalk and good electromagnetic screening are necessary. A high-pass filter removes the time-independent component from the electrical signal of the detector 13 and the latter is amplified by a high-frequency amplifier, which is carried out by a signal conditioning 14 on the detection side. The time-independent signal can be evaluated additionally. The phase-sensitive detector 15 determines the amplitude and phase of the detected signal relative to the signal that the frequency generator 3 produces. The frequency generator 3 and phase-sensitive detector 15 are combined in a network analyser.

Individual components of the measuring instrument in FIG. 1 can be controlled by a personal computer, which is also used for performing further evaluation of the measuring signals, so that finally an optical absorption coefficient and an effective optical scattering coefficient can be determined. From these it is also possible to determine other sample parameters such as particle concentration or particle size.

FIG. 2 shows outputs of a plurality of optical waveguide elements in the viewing direction towards the outputs. The plurality of optical waveguide elements are used on the one hand for coupling-in the excitation light onto the sample to be investigated and on the other hand also for coupling-out the measurement light produced in the sample from these and then feed them to the detector 13. FIG. 2 shows blunt ends of optical waveguides, which depending on the measuring task and selected measurement configuration can be used for feeding the excitation light to the sample or for receiving the measurement light from the sample. The individual optical waveguide elements corresponding to the particular measurement configuration are used by means of corresponding connection, which in its turn is effected with an optical switching device (not shown), for example a fibre-fibre switch. For example an internal optical waveguide 20 can be used for coupling-in of the excitation light, whereas the remaining optical waveguides serve for receiving the measurement light. A reversed design can also be envisaged. Furthermore, the plurality of optical waveguides can be used in succession as optical waveguides for the excitation light and optical waveguides for the measurement light. The optical switch providing the various measurement configurations can for example be effected using a translation slide. Various embodiments of said optical switching devices are known per se.

FIG. 3 shows a schematic representation with one measuring chamber 30 and a plurality of optical waveguide elements 31, whose outputs are arranged in the measuring chamber 30. Alternatively the outputs can project into the measuring chamber 30 from above.

The features of the invention disclosed in the above description, the claims and the drawing may be of importance both individually and in any combination for the realization of the invention in its various embodiments.

The invention claimed is:
1. A photon density wave spectrometer, comprising:
 a measuring chamber loaded with a sample to be measured; and
 a coupling-in/coupling-out device configured for receiving excitation light from a light source and for coupling-in on the sample to be measured in the measuring chamber and for receiving measurement light formed in the sample to be measured on account of the coupled-in excitation light and for feeding the measurement light to a detection device;

wherein the coupling-in/coupling-out device has an optical switching device and a plurality of optical waveguide elements coupling thereto with a respective optical waveguide connected by the optical switching device according to at least one selectable measurement configuration, to couple-in the excitation light corresponding to at least one selectable measurement configuration and to receive the measurement light, so that depending on a connection of an individual optical waveguide element, the excitation light and the measurement light is guided by an associated optical waveguide; wherein outputs of the several optical waveguide elements are positioned in a viewing direction towards outputs corresponding to a spiral-shaped arrangement.

2. The photon density wave spectrometer according to claim 1, wherein the outputs of the plurality of optical waveguide elements are arranged at different distances relative to a reference level transversely to the light exit direction of the excitation light from the outputs.

3. The photon density wave spectrometer according to claim 1, wherein the outputs of the plurality of optical waveguide elements are fixed in their position relative to one another at least for the at least one measurement configuration.

4. The photon density wave spectrometer according to claim 1, wherein at least one part of the outputs of the plurality of optical waveguide elements is arranged in the measuring chamber.

5. The photon density wave spectrometer according to claim 4, wherein the part of the optical waveguide elements, for which the output is arranged in the measuring chamber, is led fluid-tight through a section of the wall of the measuring chamber.

6. The photon density wave spectrometer according to claim 1, wherein the outputs of the plurality of optical waveguide elements are formed of optical waveguide outputs of the optical waveguide.

7. The photon density wave spectrometer according to claim 1, wherein the optical waveguides are formed of optical waveguides with a graded-index profile.

8. The photon density wave spectrometer according to claim 1, wherein the optical waveguides are formed of photonic crystal fibres.

9. The photon density wave spectrometer according claim 1, wherein the optical waveguides are constructed according to at least one of the following designs: deuterated optical waveguides and fluorinated optical waveguides.

10. A photon density wave spectrometer having a measuring arrangement according to claim 1.

* * * * *